United States Patent [19]

Schlegel et al.

[11] Patent Number: 5,294,741
[45] Date of Patent: Mar. 15, 1994

[54] CONTINUOUS PROCESS FOR THE PREPARATION OF SULFONYLISOCYANATES

[75] Inventors: Günter Schlegel, Liederbach; Stephen Lachhein, Hofheim am Taunus; Harald Berger, Kelkheim, all of Fed. Rep. of Germany

[73] Assignee: Hoechst Aktiengesellschaft, Frankfurt am Main, Fed. Rep. of Germany

[21] Appl. No.: 839,790

[22] Filed: Feb. 21, 1992

[30] Foreign Application Priority Data

Feb. 25, 1991 [DE] Fed. Rep. of Germany ....... 4105823

[51] Int. Cl.$^5$ ............................................. C07C 311/65
[52] U.S. Cl. ................................ 562/870; 560/350; 560/351
[58] Field of Search ............... 560/350, 351; 558/40, 558/44; 562/870

[56] References Cited

U.S. PATENT DOCUMENTS

| | | | |
|---|---|---|---|
| 3,243,448 | 3/1966 | Ernet | 560/350 |
| 3,574,740 | 4/1971 | Martin | 560/351 |
| 3,931,277 | 1/1976 | Lohaus et al. | 560/351 |

FOREIGN PATENT DOCUMENTS

| | | | |
|---|---|---|---|
| 005331 | 6/1982 | European Pat. Off. | 560/350 |
| 0131058 | 1/1985 | European Pat. Off. | 560/350 |
| 0342569 | 11/1989 | European Pat. Off. | 560/350 |
| 3132944 | 3/1983 | Fed. Rep. of Germany | 562/870 |
| 3228101 | 2/1984 | Fed. Rep. of Germany | 562/870 |
| 72-14434 | 5/1973 | Netherlands | 562/870 |

OTHER PUBLICATIONS

G. Lohaus, Chem. Ber. 105, 2751, 2799 (1972).

*Primary Examiner*—Floyd D. Higel
*Attorney, Agent, or Firm*—Curtis, Morris & Safford

[57] ABSTRACT

The invention relates to an improved process for the preparation of a compound of the formula $R^1\text{-X-SO}_2\text{-NCO}$ in which X is O or $NR^2$,
$R^1$ is alkylsulfonyl or phenyl which is optionally substituted by Hal, alkyl and/or alkoxy, and
$R^2$ is alkyl, by reacting
$R^1XH$ with $ClSO_2NCO$ to give the compound $R^1XCONHSO_2Cl$ followed by a rearrangement reaction, which comprises carrying out the process continuously in the presence or absence of an inert solvent.

20 Claims, No Drawings

CONTINUOUS PROCESS FOR THE PREPARATION OF SULFONYLISOCYANATES

DESCRIPTION

The invention relates to the field of industrial processes for the preparation of reactive compounds which can be used, for example, for the preparation of plant protection agents, such as sulfonylureas.

The present invention relates to a process for the preparation of a sulfonyl isocyanate of the formula I $$R^1-X-SO_2-N=C=O \qquad (I)$$

in which

X is O or $NR^2$, $R^1$ is $(C_1-C_4)$alkylsulfonyl or phenyl which is unsubstituted or monosubstituted or polysubstituted by radicals selected from the group comprising halogen, $(C_1-C_4)$alkyl and $C_1-C_4)$alkoxy, and $R^2$ is $C_1-C_4)$ alkyl, by reacting a compound of the formula II $$R^1-X-H \qquad (II)$$

in which

X and $R^1$ have the meanings given in formula I, with the chlorosulfonyl isocyanate of the formula III $$Cl-SO_2-N=C=O \qquad (III)$$

to give a compound of the formula IV $$R^1-X-CO-NH-SO_2-Cl \qquad (IV)$$

in which $R^1$ and X have the meanings given in formula I, and the subsequent rearrangement of the compound of the formula IV to give the compound of the formula I, which comprises carrying out the process continuously without a solvent or in the presence of an inert organic solvent.

Preferred compounds of the formula I are those in which $R^1$ is $CH_3SO_2$, X is $NR^2$ and $R^2$ is $CH_3$, or $R^1$ is 2-ethoxyphenyl and X is O.

The compounds of the formula I are known. They are used as valuable intermediates in the preparation of herbicidal sulfonylureas (U.S. Pat. No. 4,169,179; EP-A-071,958; EP-A-342,569; EP-A-0,131,258).

The compounds of the formula II are either commercially available or can be synthesized readily by methods known from the literature (DE-A-1,929,295).

It is known that the compounds of the formula I can be prepared batchwise by one- or two-step reactions to give a yield of 60 to 80% of theory (DE-A-2,257,240; G. Lohaus, Chem. Ber. 105, 2791-2799 (1972)).

A batchwise process for the preparation of 2-ethoxyphenoxysulfonyl isocyanate from chlorosulfonyl isocyanate and 2-ethoxyphenol in xylene is also known (EP-A-0,342,569). Even though the crude yield is generally high, the isolated yield of ethoxyphenoxysulfonyl isocyanate here is merely 91% of theory (see Comparison Examples I and II).

These known batchwise processes thus leave something to be desired with a view to Bulfonyl isocyanate yield and give residues of starting materials or by-products which must be disposed of. On an industrial scale, this results in substantial adverse effects from the economical as well as the ecological point of view.

The known batchwise processes require a minimum reaction time of approx. 2.5 hours; this means that the conversion of the compounds of the formula IV into the compounds of the formula I proceeds at a very slow rate. The rate of the rearrangement reaction cannot be increased at will by increasing the temperature since the sulfonyl isocyanates are thermally unstable at elevated temperatures.

All the abovedescribed shortcomings are avoided by the process according to the invention in which the sulfonyl isocyanates of the formula I are obtained in virtually quantitative yields of approx. 98% of theory or above and in such high purities that these products can be employed directly in subsequent reactions without additional purification procedures. In addition, the process is particularly simple to carry out from the point of view of procecss technology since it can be operated continuously.

For example, the process according to the invention is carried out in such a way that the compounds of the formulae II and III are reacted continuously in a first reactor to give the compounds of the formula Iv, which are then continuously pumped through a flow tube and a cascade arrangement of suitable length, where they are allowed to react. The gaseous HCl formed is preferably distilled off at the top at the end of the flow tube. In the case of a cascade arrangement, HCl can also be distilled off at some, or all, cascade steps.

1-1.2 mole equivalents of the compound of the formula III are preferably employed per mole of the compound of the formula II.

The process can be carried out without solvent or in a suitable solvent which is inert under the reaction conditions in particular to chlorosulfonyl isocyanate, such as halogenated or nitrogenated aromatic hydrocarbons, for example chlorobenzene and dichlorobenzene, or nitrobenzene.

The reaction temperature for the rearrangement reaction of the compound of the formula IV in the flow tube or in the cascade arrangement is preferably between 100° and 150° C.

The reaction temperature for the synthesis of the compound of the formula IV is preferably between 20° and 100° C., but, in particular, it can also be higher, for example up to 150° C. If a first reactor is used, this temperature can be adjusted readily.

Alternatively, a process can be selected in which the compounds of the formulae II and III together are pumped simultaneously via 2 separate pumps into a flow tube where they are first mixed, for example in a static mixer. Both the reaction of the compounds of the formulae II and III as well as the rearrangement reaction to give compounds of the formula I subsequently take place in the flow tube. It may be advantageous to establish a temperature gradient in the flow tube or to pass through a succession of two or more tubes which have different jacket temperature. The tubes may be packed and may be filled completely or partially with the reaction mixture.

In a further embodiment of the process, the compounds of the formulae II and III are metered simultaneously or, after a first reaction to give the compound of the formula IV, said compound IV from the top into a vertical reaction column (for example packed distillation column) and organic solvent is simultaneously fed in at the bottom, and the product is distilled off at the top together with the HCl.

* said compound IV

In a preferred embodiment, the continuous process is carried out in such a way that the compound of the formula IV is synthesized in a first reactor, and the reaction mixture obtained is allowed to flow continuously through a cascade arrangement of a plurality of relatively small reaction vessels, and evolving HCl is distilled off during each cascade step. This process is also preferably carried out at a temperature gradient.

Another preferred arrangement is a combination of a plurality of the above process embodiments, where the compounds IV are continuously formed in the first reactor and the reaction mixture is then first allowed to flow continuously into a smaller reaction vessel and subsequently through a flow tube of a suitable length.

The reactor residence time during the rearrangement reaction of the compound of the formula IV is preferably 30 to 90 minutes, in particular 45 to 75 minutes. It depends on the dimension of the reactors and the flow rates of the reactants.

In the case of the rapid first reaction, a very brief reactor residence time may be selected, for example 1 to 10 minutes.

The sulfonyl isocyanates prepared can be isolated by customary methods, for example by distillation under reduced pressure.

The process according to the invention allows the sulfonyl isocyanates of the formula (I) to be prepared on an industrial scale in a surprisingly high yield under conditions which are easy to control. The process is particularly surprising with a view to the relatively slow rearrangement reaction of the compound of the formula IV, which, if carried out in a batchwise process, requires residence times of the order of hours. The slower a reaction proceeds, the fewer generally the advantages which are to be achieved when a batchwise process is abandoned in favor of a continuous process. However, the process according to the invention allows an unexpectedly higher yield under reaction conditions which are easy to control.

EXAMPLE 1

Methanesulfonylmethylaminosulfonyl isocyanate 5 l of dry chlorobenzene are introduced at 60° C. into a 20 l four-necked flask, and 15.1 kg of N-methylmethanesulfonamide dissolved in 20 kg of chlorobenzene and 20.5 kg of chlorosulfonyl isocyanate, dissolved in 15 kg of chlorobenzene, are metered in continuously by in each case a separate pump in the course of 15 hours. During this addition, the reaction solution is pumped from the reaction vessel via an ascending pipe at a rate of approx. 5 kg/hour into a vertical flow tube of 4 m length and 4 cm diameter. The jacket temperature of the flow tube is 140°–150° C. The hydrochloric acid which forms is distilled off at the top, and the reaction solution is allowed to run off continuously.

The four-necked flask and the flow tube are rinsed with 20 kg of chlorobenzene, the solvent chlorobenzene is removed from the flow filtrate by means of distillation, and 29.6 kg of methanesulfonylmethylaminosulfonyl isocyanate of a content of 98.2% by weight are then obtained, which corresponds to a yield of 98.0% of theory.

The boiling point of a representative sample was 95°–97° C./0.13 mbar. With a view to identity and purity, the $^1$H NMR spectrum of the crude product corresponds to a distilled sample from a process described in the literature.

EXAMPLE 2

2-Ethoxyphenoxysulfonyl isocyanate 6.9 kg of 2-ethoxyphenol and 7.2 kg of chlorosulfonyl isocyanate are metered at a uniform rate into the first flask of a cascade arrangement filled with chlorobenzene and consisting of three 1 l four-necked flasks provided with overflow and distillation head in the course of 6 hours, and the bottom product of the third flask is collected in a storage container. The apparatus is kept under a nitrogen atmosphere. The first flask is kept at a bath temperature of 90° C., the second one at a bath temperature of 150° C. and the third one at a bath temperature of 165° C. During the reaction which proceeds under vigorous reflux conditions, the HCl which forms is expelled from the head of the flask into a suitable receiving vessel, and small amounts of chlorobenzene which has been distilled off are recycled to flask 1. When all the starting materials have passed through, the apparatus is washed with 5 l of chlorobenzene and emptied into the storage container. Removal of the solvent by distillation gives 12.3 kg of residue which, according to HPLC analysis (after derivatization) contains 96.2% by weight of 2-ethoxyphenoxysulfonyl isocyanate, which corresponds to a yield of 97.3% of theory. A sample distilled at 140° C./ 0.67 mbar has a refractive index of $n_D^{25} = 1.5045$ and also agrees with material prepared by known processes with regard to the $^1$H NMR spectrum.

COMPARISON EXAMPLE 1

Synthesis of 2-ethoxyphenoxysulfonyl isocyanate in xylene following EP-A-342,569

55.2 g of 2-ethoxyphenol are dissolved in 200 ml of xylene and reacted with 67.9 g of chlorosulfonyl isocyanate at 25° C.. The reaction mixture is heated to 140° C. and refluxed for 2.5 hours, during which process HCl is formed. After the solvent has been removed by distillation, 97.2 g of an oil are obtained which has a purity of 91% based on weight, corresponding to a yield of 91% of theory.

COMPARISON EXAMPLE II

Synthesis of 2-ethoxyphenyl isocyanate in chlorobenzene as in EP 342,569

55.2 g of 2-ethoxyphenol are dissolved in 200 ml of chlorobenzene and reacted with 67.9 g of chlorosulfonyl isocyanate at 25° C. The reaction mixture is heated to 132° C. and refluxed for 2.5 hours, during which process HCl is formed. After the solvent has been distilled off, 91.8 g of an oil containing 94.8% by weight of the desired product are obtained, corresponding to a yield of 89.5% of theory.

We claim:

1. A process for the preparation of a compound of the formula I

$$R^1-X-SO_2-N=C=O \qquad (I)$$

in which

X is O or NR$^2$,

R$^1$ is (C$_1$–C$_4$) alkylsulfonyl or phenyl which is unsubstituted or monosubstituted or polysubstituted by radicals selected from the group consisting of halogen, (C$_1$–C$_4$) alkyl and (C$_1$–C$_4$)-alkoxy, and R$^2$ is (C$_1$–C$_4$) alkyl, by reacting a compound of the formula II $$R^1-X-H \quad (II)$$

in which X and $R^1$ have the meanings given in formula I, with the chlorosulfonyl isocyanate of the formula III $$Cl-SO_2-N=C=O \quad (III)$$

to give a compound of the formula IV $$R^1-X-CO-NH-SO_2-Cl \quad (IV)$$

in which $R^1$ and X have the meaning given in formula I, and the subsequent rearrangement of the compound of the formula IV to give the compound of the formula I, which comprises carrying out the process continuously, wherein the temperature during said rearrangement is from 90° C. to 165° C. and the reactor residence time during said rearrangement is from 30 to 90 minutes, without a solvent or in the presence of an inert organic solvent.

2. The process as claimed in claim 1, wherein the reaction temperature for the reaction of the compounds of the formulae II and III is between 20° and 150° C.

3. The process as claimed in claim 2, wherein the temperature is between 20° and 100° C.

4. The process as claimed in claim 1, wherein the reaction temperature for the rearrangement reaction of the compound of the formula IV is 100° to 150° C.

5. The process as claimed in claim 1, wherein the solvent employed is a halogenated or nitrogenated aromatic hydrocarbon.

6. The process as claimed in claim 5, wherein chlorobenzene is used as the solvent.

7. The process as claimed in claim 1, wherein the process is carried out with or without a first reactor in a flow tube, a cascade arrangement or a packed reaction column, or a combination of these.

8. The process as claimed in claim 7, wherein the entire process is carried out in a flow tube.

9. The process as claimed in claim 7, wherein, in the process, a first reactor is used for reacting the compounds of the formulae II and III to give the compound of the formula IV and a sequence of cascades with a plurality of reaction vessels is used for the rearrangement reaction of the compound of the formula IV, where each subsequent reaction vessel has a higher temperature than the preceding one.

10. The process as claimed in claim 1, wherein the reactor residence time is 45 to 75 minutes.

11. The process as claimed in claim 1, wherein 1 to 1.2 moles of compound of the formula III are employed per mole of compound of the formula II.

12. The process as claimed in claim 1, wherein $R^1$ is $CH_3SO_2$, X is $NR^2$ and $R^2$ is $CH_3$.

13. The process as claimed in claim 1, wherein $R^1$ is 2-ethoxyphenyl and X is O.

14. The process as claimed in claim 3, wherein the reaction temperature for the rearrangement reaction of the compound of formula IV is 100° to 150° C.

15. The process as claimed in claim 14, wherein 1 to 1.2 moles of compound III are employed per mole of compound II.

16. The process as claimed in claim 15, wherein $R^1$ is $CH_3SO_2$, X is $NR^2$ and $R^2$ is $CH_3$.

17. The process as claimed in claim 15, wherein $R^1$ is 2-ethoxyphenyl and X is O.

18. The process as claimed is claim 14, wherein the reactor residence time for rearrangement is 45 to 75 minutes.

19. The process as claimed in claim 18, wherein the solvent employed is a halogenated or nitrogenated aromatic hydrocarbon.

20. The process as claimed in claim 19, wherein 1 to 1.2 moles of compound III is employed per mole of compound II.

* * * * *